(12) United States Patent
Mansfield et al.

(10) Patent No.: US 7,572,818 B2
(45) Date of Patent: Aug. 11, 2009

(54) 2-PYRIDYLETHYLBENZAMIDE DERIVATIVE

(75) Inventors: Darren James Mansfield, Lyons (FR); Tracey Cooke, St Albans (GB); Peter Stanley Thomas, Cambridge (GB); Pierre-Yves Coqueron, Lyons (FR); Jean-Pierre Vors, Lyons (FR); Geoffrey Gower Briggs, Herts (GB); Hélène Lachaise, Lyons (FR); Heiko Rieck, Sainte Foy les Lyons (FR); Philippe Desbordes, Lyons (FR); Marie-Claire Grosjean-Cournoyer, Curis Au Mont d'Or (FR)

(73) Assignee: Bayer Cropscience S.A. (FR)

( * ) Notice: Subject to any disclaimer, the term of this patent is extended or adjusted under 35 U.S.C. 154(b) by 492 days.

(21) Appl. No.: 10/524,345

(22) PCT Filed: Aug. 8, 2003

(86) PCT No.: PCT/EP03/09516

§ 371 (c)(1),
(2), (4) Date: Feb. 11, 2005

(87) PCT Pub. No.: WO2004/016088

PCT Pub. Date: Feb. 26, 2004

(65) Prior Publication Data

US 2005/0234110 A1     Oct. 20, 2005

(30) Foreign Application Priority Data

Aug. 12, 2002 (EP) .................... 02356159
Apr. 29, 2003 (FR) .................... 03 05233

(51) Int. Cl.
*A61K 31/44* (2006.01)
(52) U.S. Cl. .................... 514/357; 546/337
(58) Field of Classification Search ............ 546/330, 546/337; 504/141, 149; 514/357
See application file for complete search history.

(56) References Cited

FOREIGN PATENT DOCUMENTS

WO         9942447       *  8/1999
WO    WO 01/11965           2/2001

OTHER PUBLICATIONS

International Search Report dated Jan. 27, 2004.
* cited by examiner

*Primary Examiner*—Janet L. Andres
*Assistant Examiner*—Binta Robinson
(74) *Attorney, Agent, or Firm*—Ostrolenk Faber LLP

(57) ABSTRACT

Compound of general formula (I) in which p is an integer equal to 1, 2, 3 or 4; q is an integer equal to 1, 2, 3, 4 or 5; each substituent X is chosen, independently of the others, as being halogen, alkyl or haloalkyl, at least one of the substituents being a haloalkyl; each substituent Y is chosen, independently of the others, as being halogen, alkyl, alkenyl, alkynyl, haloalkyl, alkoxy, amino, phenoxy, alkylthio, dialkylamino, acyl, cyano, ester, hydroxy, aminoalkyl, benzyl, haloalkoxy, halosulphonyl, halothioalkyl, alkoxyalkenyl, alkylsulphonamide, nitro, alkylsulphonyl, phenylsulphonyl or benzylsulphonyl; as to the N-oxides of 2-pyridine thereof; with the exception of N-{2-[3-chloro-5-(trifluoromethyl)-2-pyridinyl]-ethyl}-2,6-dichlorobenzamide. Method for preparing the compound of general formula (I). Fungicidal composition comprising the compound of general formula (I). Method for treating phytopathogenic diseases.

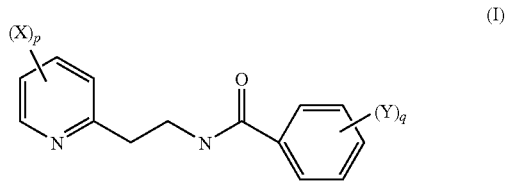

(I)

16 Claims, No Drawings

2-PYRIDYLETHYLBENZAMIDE DERIVATIVE

CROSS REFERENCE TO RELATED APPLICATIONS

The present application is a 35 U.S.C. § 371 national phase conversion of International Application No. PCT/EP2003/009516, filed Aug. 8, 2003, which claims priority of European Application No. 02356159.0 filed Aug. 12, 2002 and French Application No. 0305233 filed Apr. 29, 2003.

The present invention relates to novel fungicidal compounds, to the method for preparing them, to the fungicidal compositions comprising these compounds, and also to their use in the agricultural field as fungicides.

Patent Application WO 01/11965 describes a broad family of fungicidal compounds of general formula encompassing the compounds of the present invention. However, the said compounds are not described in that patent application and their activity as a fungicide was not tested.

It is however always useful, in the agricultural field, to use compounds which are more active than those already known to those skilled in the art, with the aim of decreasing the amounts of active material to be used by the farmer, whilst at the same time maintaining an effectiveness at least equivalent to the already known compounds.

It has now been discovered that a certain number of compounds, selected from a broad family of compounds, possess the above mentioned advantages.

A subject of the present invention is therefore a family of fungicidal compounds of general formula (I):

(I)

in which:
p is an integer equal to 1, 2, 3 or 4;
q is an integer equal to 1, 2, 3, 4 or 5;
each substituent X is chosen, independently of the others, as being halogen, alkyl or haloalkyl, at least one of the substituents being a haloalkyl;
each substituent Y is chosen, independently of the others, as being halogen, alkyl, alkenyl, alkynyl, haloalkyl, alkoxy, amino, phenoxy, alkylthio, dialkylamino, acyl, cyano, ester, hydroxy, aminoalkyl, benzyl, haloalkoxy, halosulphonyl, halothioalkyl, alkoxyalkenyl, alkylsulphonamide, nitro, alkylsulphonyl, phenylsulphonyl or benzylsulphonyl;
as to the N-oxides of 2-pyridine thereof;
with the exception of N-{2-[3-chloro-5-(trifluoromethyl)-2-pyridinyl]ethyl}-2,6-dichlorobenzamide.

In the context of the present invention, the substituents X of the 2-pyridine and the substituents Y of the benzene ring will be indexed in order to facilitate understanding. Thus, for example, if p is equal to 2 and q is equal to 1, the substituents termed "X" will be denoted by $X^1$ and $X^2$ and the substituent termed "Y" will be denoted by $Y^1$.

For the purposes of the present invention, halogen means chlorine, bromine, iodine or fluorine.

For the purposes of the present invention, each of the alkyl or acyl radicals present in the molecule contains from 1 to 10 carbon atoms, preferentially from 1 to 7 carbon atoms, more preferentially from 1 to 5 carbon atoms, and may be linear or branched.

For the purposes of the present invention, each of the alkenyl or alkynyl radicals present in the molecule contains from 2 to 10 carbon atoms, preferentially from 2 to 7 carbon atoms, more preferentially from 2 to 5 carbon atoms, and may be linear or branched.

The present invention relates to compound of general formula (I). Preferentially, compounds of general formula (I) have the following characteristics, taken individually or in combination:
p is chosen equal to 2, the substituents $X^1$ and $X^2$ being positioned as follows:

q is chosen equal to 1 or 2, the substituent(s) Y being positioned in the ortho position of the benzene ring.

A preferred subfamily of compounds according to the invention consists of the compounds corresponding to general formula (I')

(I')

X and Y being as defined above. More preferably, $X^1$ is chosen as being halogen and $X^2$ is chosen as being haloalkyl.

Another preferred subfamily of compounds according to the invention consists of the compounds corresponding to general formula (I"):

(I")

the substituents X and Y being as defined above. More preferably, compound of general formula (I") according to the present invention have the following characteristics, taken individually or in combination:
$X^1$ is chosen as being halogen and $X^2$ is chosen as being haloalkyl;
$Y^1$ is chosen as being halogen or haloalkyl.
More preferably, the haloalkyl group is chosen as being trifluoromethyl.

Even more preferably, a subject of the present invention is the following compounds:

N-{2-[3-chloro-5-(trifluoromethyl)-2-pyridinyl]ethyl}-2-trifluoromethylbenzamide;

N-{2-[3-chloro-5-(trifluoromethyl)-2-pyridinyl]ethyl}-2-iodobenzamide;

N-{2-[3-chloro-5-(trifluoromethyl)-2-pyridinyl]ethyl}-2-bromobenzamide.

The present invention also relates to a process for the preparation of the compound of general formula (I). Thus, according to a further aspect of the present invention there is provided a process for the preparation of compound of formula (I) as defined above which comprises:

a first step consisting in reacting, in the presence of a base in an aprotic polar solvent, a compound of general formula (Ia) in order to substitute it selectively in the 2-position:

either with a group of the alkyl cyanoacetate type (NC—CH$_2$—CO$_2$Alk) to produce a compound of general formula (Ib) according to the following reaction scheme:

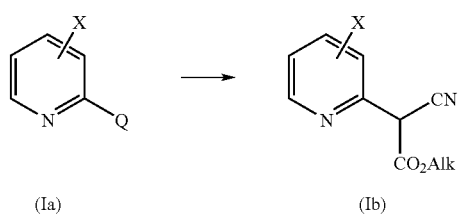

(Ia)    (Ib)

where:

X is as previously defined;

Alk represents an alkyl radical;

Q is a nucleofugal radical, preferably chosen to be a halogen or trifluoromethanesulphonate;

the compound of general formula (Ib) thus obtained then undergoing dealkyloxy-carbonylation in the presence of an alkali metal halide, such as Li-halogen, K-halogen or Na-halogen, at the reflux of a water/dimethyl sulphoxide mixture, according to the Krapcho reaction described in A.P. *Synthesis*, 1982, 805, 893, to produce the compound of general formula (Ic) according to the following reaction scheme:

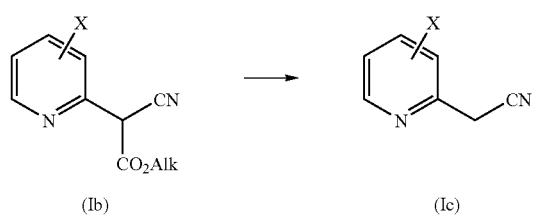

(Ib)    (Ic)

sodium halide will preferentially be used in the context of the present invention;

or with acetonitrile to directly produce the compound of general formula (Ic) according to the following reaction scheme:

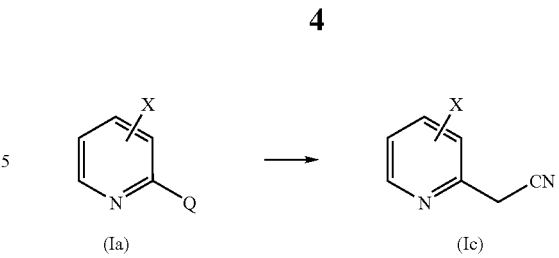

(Ia)    (Ic)

a second step consisting in the reduction of the compound of general formula (Ic) to pyridylethanamine of general formula (Id) (or its corresponding ammonium salt depending on whether or not the medium is acid) under hydrogen pressure in the presence of a metal catalyst in a protic solvent according to the following reaction scheme:

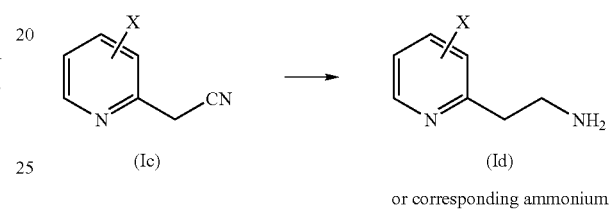

(Ic)    (Id)

or corresponding ammonium a third step consisting in converting the compound of general formula (Id) to a compound of general formula (I) by reaction with a benzoyl halide in the presence of a base according to the following reaction scheme:

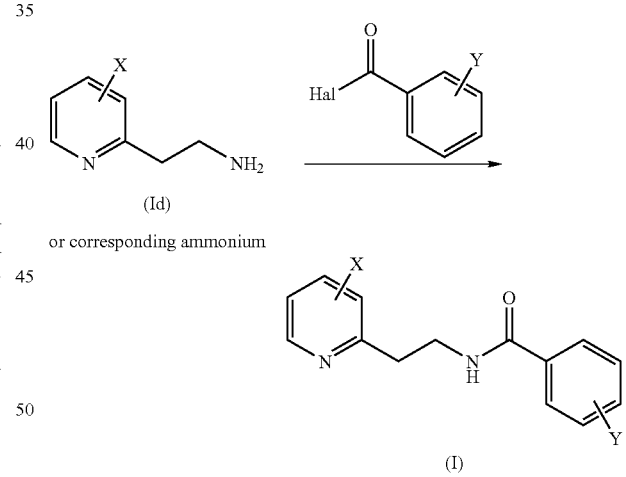

(I)

The second step of the above described process is conducted in the presence of a metal catalyst. Preferably, the metal catalyst is chosen as being a nickel-, platinum- or palladium-based catalyst.

The third step of the above mentioned process is conducted in the presence of a benzoyl halide. Preferably, the benzoyl halide is chosen as being benzoyl chloride.

From compound of general formula (I) obtained by virtue of the method of preparation described above, those skilled in the art will be able to prepare, by virtue of methods known to them, the N-oxide derivatives of 2-pyridine. For example, the compound of general formula (I) obtained by virtue of the method according to the present invention may be treated with an excess of meta-chloroperbenzoic acid (also called m-CPBA) in the presence of a solvent, which may be chloroform, at a temperature which may range from 60 to 80° C.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity: The mixtures with other fungicides are particularly advantageous.

The fungicidal compositions of the present invention can be used to curatively or preventively control the phytopathogenic fungi of crops. Thus, according to a further aspect of the present invention, there is provided a method for curatively or preventively controlling the phytopathogenic fingi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fingi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants protected by the method according to the present invention, mention may be made of:

wheat, as regards controlling the following seed diseases:
fusaria (*Microdochium nivale* and *Fusarium roseum*), stinking smut (*Tilletia caries, Tilletia controversa* or *Tilletia indica*), *septoria* disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis forma specie tritici*), rusts (*Puccinia striiformis* and *Puccinia recondita*) and *septoria* diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forma specie hordei*), dwarf leaf rust (*Puccinia hordei*) and leaf blotch (*Rhynchosporium secalis*);

potato, as regards controlling tuber diseases (in particular *Helminthosporium solani, Phoma tuberose, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Sclerotinia sclerotiorum*;

corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola*;

forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), *septoria* leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: *monilia* disease (*Monilia fructigenae, M laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: *cercospora* blight (*Cercospora beticola*), powdery mildew (*Erysiphe beticola*), leaf spot (*Ramularia beticola*).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

The aspects of the present invention will now be illustrated with reference to the following tables of compounds and examples. The following Tables A and B illustrate in a non-limiting manner examples of fungicidal compounds according to the present invention. In the following Examples, M+1 means the molecular ion peak, plus or minus 1 a.m.u. (atomic mass units) respectively, as observed in mass spectroscopy and M (ApcI+) means the molecular ion peak as it was found via positive atmospheric pressure chemical ionisation in mass spectroscopy.

TABLE A

| Composé n° | X¹ | X² | X³ | X⁴ | Y¹ | Y² | Y³ | Y⁴ | Y⁵ | M + 1 |
|---|---|---|---|---|---|---|---|---|---|---|
| A-1 | H | CF₃ | H | H | CF₃ | H | H | H | H | 363 |
| A-2 | Cl | CF₃ | H | H | Cl | H | H | H | H | 363 |
| A-3 | Cl | CF₃ | H | H | H | H | H | Cl | Cl | 397 |
| A-4 | Cl | CF₃ | H | H | F | H | H | H | H | 347 |
| A-5 | Cl | CF₃ | H | H | F | H | H | F | H | 365 |
| A-6 | Cl | CF₃ | H | H | Cl | H | H | Cl | H | 397 |
| A-7 | Cl | CF₃ | H | H | OMe | H | H | H | H | 359 |
| A-8 | Cl | CF₃ | H | H | OMe | OMe | H | H | H | 389 |
| A-9 | Cl | CF₃ | H | H | Me | H | H | H | H | 343 |
| A-10 | Cl | CF₃ | H | H | H | H | F | H | H | 347 |
| A-11 | Cl | CF₃ | H | H | H | H | Cl | H | H | 363 |
| A-12 | Cl | CF₃ | H | H | H | H | OMe | H | H | 359 |
| A-13 | Cl | CF₃ | H | H | H | H | OMe | OMe | H | 389 |
| A-14 | Cl | CF₃ | H | H | H | H | OMe | H | OMe | 389 |
| A-15 | Cl | CF₃ | H | H | H | H | H | F | H | 347 |
| A-16 | Cl | CF₃ | H | H | H | H | H | OMe | H | 359 |
| A-17 | Cl | CF₃ | H | H | H | H | H | OBu | H | 401 |
| A-18 | Cl | CF₃ | H | H | H | H | H | C(CH₃)₃ | H | 397 |
| A-19 | Cl | CF₃ | H | H | H | H | H | Me | H | 343 |
| A-20 | Cl | CF₃ | H | H | CF₃ | H | H | H | H | 397 |
| A-21 | Cl | CF₃ | H | H | H | H | H | Et | H | 357 |
| A-22 | Cl | CF₃ | H | H | H | H | H | Pr | H | 371 |
| A-23 | Cl | CF₃ | H | H | H | H | H | Bu | H | 385 |
| A-24 | Cl | CF₃ | H | H | H | H | H | C₅H₁₁ | H | 399 |
| A-25 | Cl | CF₃ | H | H | F | F | H | H | H | 365 |
| A-26 | Cl | CF₃ | H | H | H | H | Me | H | H | 343 |
| A-27 | Cl | CF₃ | H | H | H | H | CH₂Cl | H | H | 377 |
| A-28 | Cl | CF₃ | H | H | H | H | CF₃ | H | H | 397 |
| A-29 | Cl | CF₃ | H | H | NO₂ | H | H | H | H | 374 |
| A-30 | Cl | CF₃ | H | H | H | H | NO₂ | H | H | 374 |
| A-31 | Cl | CF₃ | H | H | H | H | H | NO₂ | H | 374 |
| A-32 | Cl | CF₃ | H | H | H | H | Cl | H | Cl | 396 |
| A-33 | Cl | CF₃ | H | H | F | H | H | H | F | 365 |
| A-34 | Cl | CF₃ | H | H | H | H | H | F | F | 365 |
| A-35 | Cl | CF₃ | H | H | H | H | F | H | F | 365 |
| A-36 | Cl | CF₃ | H | H | H | H | CN | H | H | 354 |
| A-37 | Cl | CF₃ | H | H | Me | Me | H | Me | H | 371 |
| A-38 | Cl | CF₃ | H | H | H | H | NO₂ | Me | H | 388 |
| A-39 | Cl | CF₃ | H | H | H | H | H | CO₂Me | H | 387 |
| A-40 | Cl | CF₃ | H | H | F | F | F | H | H | 383 |
| A-41 | Cl | CF₃ | H | H | F | H | H | F | F | 383 |
| A-42 | Cl | CF₃ | H | H | F | F | H | F | H | 383 |
| A-43 | Cl | CF₃ | H | H | F | H | F | F | F | 401 |
| A-44 | Cl | CF₃ | H | H | F | Cl | H | H | H | 382 |
| A-45 | Cl | CF₃ | H | H | I | H | H | H | H | 455 |
| A-46 | Cl | CF₃ | H | H | Br | H | H | H | H | 407 |
| A-47 | Cl | CF₃ | H | H | CF3 | H | F | H | H | 413 |
| A-48 | Cl | CF₃ | H | H | Cl | H | Cl | H | H | 397 |
| A-49 | Cl | CF₃ | H | H | Cl | H | H | H | Cl | 397 |
| A-50 | Cl | CF₃ | H | H | NHCH₃ | H | H | H | H | 358 |
| A-51 | Cl | CF₃ | H | H | OMe | H | OMe | H | H | 389 |
| A-52 | Cl | CF₃ | H | H | OH | H | H | H | H | 345 |
| A-53 | Cl | CF₃ | H | H | OH | H | Me | H | H | 359 |
| A-54 | Cl | CF₃ | H | H | OH | H | H | Cl | H | 379 |
| A-55 | Cl | CF₃ | H | H | OH | H | H | OMe | H | 375 |
| A-56 | Cl | CF₃ | H | H | OH | H | H | Me | H | 359 |
| A-57 | Cl | CF₃ | H | H | OH | H | H | H | F | 363 |
| A-58 | Cl | CF₃ | H | H | OH | H | H | H | OMe | 375 |
| A-59 | Cl | CF₃ | H | H | OH | H | H | H | Me | 359 |
| A-60 | Cl | CF₃ | H | H | Me | H | Me | H | H | 357 |
| A-61 | Cl | CF₃ | H | H | Me | H | H | Me | H | 357 |
| A-62 | Cl | CF₃ | H | H | Me | H | H | H | Me | 357 |
| A-63 | Cl | CF₃ | H | H | OH | H | Cl | H | H | 379 |

TABLE A-continued

| Composé n° | X¹ | X² | X³ | X⁴ | Y¹ | Y² | Y³ | Y⁴ | Y⁵ | M + 1 |
|---|---|---|---|---|---|---|---|---|---|---|
| A-64 | Cl | CF₃ | H | H | F | H | Cl | H | H | 381 |
| A-65 | Cl | CF₃ | H | H | OH | F | H | H | H | 363 |
| A-66 | Cl | CF₃ | H | H | Me | H | Cl | H | H | 377 |
| A-67 | Cl | CF₃ | H | H | Me | H | F | H | H | 361 |
| A-68 | Cl | CF₃ | H | H | OH | H | H | F | H | 363 |
| A-69 | Cl | CF₃ | H | H | F | H | H | H | Cl | 381 |
| A-70 | Cl | CF₃ | H | H | Me | H | OH | H | H | 359 |
| A-71 | Cl | CF₃ | H | H | Br | H | H | H | OMe | 436 |
| A-72 | Cl | CF₃ | H | H | CF₃ | H | H | H | CF3 | 465 |
| A-73 | Cl | CF₃ | H | H | CF₃ | H | H | F | H | 415 |
| A-74 | Cl | CF₃ | H | H | CF₃ | H | H | CF₃ | H | 465 |
| A-75 | Cl | CF₃ | H | H | F | CF3 | Cl | H | H | 449 |
| A-76 | Cl | CF₃ | H | H | PhCH₂ | H | H | H | H | 419 |
| A-77 | Cl | CF₃ | H | H | Me | H | NO₂ | H | H | 388 |
| A-78 | Cl | CF₃ | H | H | Me | H | NO₂ | H | NO₂ | 433 |
| A-79 | Cl | CF₃ | H | H | Me | H | H | H | NO₂ | 388 |
| A-80 | Cl | CF₃ | H | H | Me | H | H | Br | H | 421 |
| A-81 | Cl | CF₃ | H | H | Me | H | OMe | H | H | 373 |
| A-82 | Cl | CF₃ | H | H | OMe | H | OMe | OMe | H | 419 |
| A-83 | Cl | CF₃ | H | H | OMe | H | H | OMe | H | 389 |
| A-84 | Cl | CF₃ | H | H | OMe | H | H | OMe | OMe | 419 |
| A-85 | Cl | CF₃ | H | H | OMe | H | H | H | OMe | 389 |
| A-86 | Cl | CF₃ | H | H | OEt | H | H | H | H | 373 |
| A-87 | Cl | CF₃ | H | H | OMe | H | H | Cl | H | 393 |
| A-88 | Cl | CF₃ | H | H | OMe | H | H | H | Cl | 393 |
| A-89 | Cl | CF₃ | H | H | OCF3 | H | H | H | H | 413 |
| A-90 | Cl | CF₃ | H | H | OMe | H | H | H | F | 377 |
| A-91 | Cl | CF₃ | H | H | OPr | H | H | H | H | 387 |
| A-92 | Cl | CF₃ | H | H | OMe | H | H | H | t-Bu | 415 |
| A-93 | Cl | CF₃ | H | H | Cl | H | H | H | Br | 441 |
| A-94 | Cl | CF₃ | H | H | I | H | I | H | I | 397 |
| A-95 | Cl | CF₃ | H | H | Cl | H | NO₂ | H | H | 408 |
| A-96 | Cl | CF₃ | H | H | Cl | H | H | NO₂ | H | 408 |
| A-97 | Cl | CF₃ | H | H | Cl | H | H | H | NO₂ | 408 |
| A-98 | Cl | CF₃ | H | H | Cl | H | H | H | SO₂F | 445 |
| A-99 | Cl | CF₃ | H | H | Cl | H | H | H | SMe | 409 |
| A-100 | Cl | CF₃ | H | H | Br | H | H | H | Cl | 441 |
| A-101 | Cl | CF₃ | H | H | Cl | H | NO₂ | H | Cl | 442 |
| A-102 | Cl | CF₃ | H | H | Br | H | H | H | Br | 485 |
| A-103 | Cl | CF₃ | H | H | Cl | H | Cl | H | Cl | 431 |
| A-104 | Cl | CF₃ | H | H | Cl | H | H | H | CF3 | 431 |
| A-105 | Cl | CF₃ | H | H | Br | H | NO₂ | H | H | 452 |
| A-106 | Cl | CF₃ | H | H | Cl | H | H | Cl | F | 415 |
| A-107 | Cl | CF₃ | H | H | Cl | H | H | F | F | 399 |
| A-108 | Cl | CF₃ | H | H | Cl | H | OMe | OMe | H | 423 |
| A-109 | Cl | CF₃ | H | H | Br | H | H | H | NO₂ | 452 |
| A-110 | Cl | CF₃ | H | H | Br | H | H | Cl | H | 441 |
| A-111 | Cl | CF₃ | H | H | Br | H | Cl | H | H | 441 |
| A-112 | Cl | CF₃ | H | H | F | Br | H | H | H | 425 |
| A-113 | Cl | CF₃ | H | H | Cl | F | F | H | H | 399 |
| A-114 | Cl | CF₃ | H | H | Et | H | H | H | H | 357 |
| A-115 | Cl | CF₃ | H | H | Me | H | H | Me | CO₂Et | 429 |
| A-116 | Cl | CF₃ | H | H | Me | H | Me | H | Cl | 391 |
| A-117 | Cl | CF₃ | H | H | Me | H | H | F | H | 361 |
| A-118 | Cl | CF₃ | H | H | Me | H | Cl | F | H | 395 |
| A-119 | Cl | CF₃ | H | H | O—CF₂—CHFCl | H | H | Cl | H | 495 |
| A-120 | Cl | CF₃ | H | H | O-allyl | H | H | Cl | H | 419 |
| A-121 | Cl | CF₃ | H | H | O-allyl | H | H | H | H | 385 |
| A-122 | Cl | CF₃ | H | H | Br | H | F | H | H | 425 |
| A-123 | Cl | CF₃ | H | H | Cl | H | Me | F | Me | 409 |
| A-124 | Cl | CF₃ | H | H | Cl | F | Me | H | H | 395 |
| A-125 | Cl | CF₃ | H | H | Cl | H | F | Cl | H | 415 |

TABLE A-continued

| Composé n° | X¹ | X² | X³ | X⁴ | Y¹ | Y² | Y³ | Y⁴ | Y⁵ | M + 1 |
|---|---|---|---|---|---|---|---|---|---|---|
| A-126 | Cl | CF₃ | H | H | Cl | H | H | CF3 | H | 431 |
| A-127 | Cl | CF₃ | H | H | SMe | H | H | Cl | H | 409 |
| A-128 | Cl | CF₃ | H | H | SO₂Me | H | H | Cl | H | 441 |
| A-129 | Cl | CF₃ | H | H | Br | H | H | NO₂ | H | 452 |
| A-130 | Cl | CF₃ | H | H | Cl | H | H | SO₂Me | H | 441 |
| A-131 | Cl | CF₃ | H | H | Cl | H | H | CN | H | 388 |
| A-132 | Cl | CF₃ | H | H | Cl | H | Cl | Cl | H | 431 |
| A-133 | Cl | CF₃ | H | H | SO₂Me | H | H | Br | H | 485 |
| A-134 | Cl | CF₃ | H | H | Br | H | H | H | Me | 421 |
| A-135 | Cl | CF₃ | H | H | CF3 | H | H | SO₂NMe₂ | H | 504 |
| A-136 | Cl | CF₃ | H | H | Cl | H | OH | SO₂Me | H | 457 |
| A-137 | Cl | CF₃ | H | H | Br | H | H | SO₂Me | H | 485 |
| A-138 | Cl | CF₃ | H | H | CF₃ | H | H | SO₂Me | H | 475 |
| A-139 | Cl | CF₃ | H | H | SO₂Me | H | H | CF3 | H | 475 |
| A-140 | Cl | CF₃ | H | H | SMe | H | H | F | H | 393 |
| A-141 | Cl | CF₃ | H | H | H | H | Br | Cl | H | 441 |
| A-142 | Cl | CF₃ | H | H | Me | H | H | SMe | H | 389 |
| A-143 | Cl | CF₃ | H | H | SMe | H | H | CF₃ | H | 443 |
| A-144 | Cl | CF₃ | H | H | SMe | H | Cl | Cl | H | 443 |
| A-145 | Cl | CF₃ | H | H | Cl | H | H | SMe | H | 409 |
| A-146 | Cl | CF₃ | H | H | SMe | H | Br | Cl | H | 487 |
| A-147 | Cl | CF₃ | H | H | H | H | CF3 | Cl | H | 431 |
| A-148 | Cl | CF₃ | H | H | SMe | H | OMe | F | H | 423 |
| A-149 | Cl | CF₃ | H | H | F | H | OMe | F | H | 395 |
| A-150 | Cl | CF₃ | H | H | Br | H | H | SMe | H | 453 |
| A-151 | Cl | CF₃ | H | H | iPr | H | Br | H | H | 449 |
| A-152 | Cl | CF₃ | H | H | Et | H | H | Br | H | 435 |
| A-153 | Cl | CF₃ | H | H | SMe | H | H | Br | H | 453 |
| A-154 | Cl | CF₃ | H | H | Br | H | OMe | Br | H | 515 |
| A-155 | Cl | CF₃ | H | H | SO₂Me | H | F | Cl | H | 459 |
| A-156 | Cl | CF₃ | H | H | NO₂ | H | H | Me | Me | 402 |
| A-157 | Cl | CF₃ | H | H | SMe | H | O—CH₂—CF₂ | Br | H | 533 |
| A-158 | Cl | CF₃ | H | H | H | H | Br | I | H | 533 |
| A-159 | Cl | CF₃ | H | H | F | H | SO₂NMe₂ | F | H | 472 |
| A-160 | Cl | CF₃ | H | H | H | H | NO₂ | Me | Me | 402 |
| A-161 | Cl | CF₃ | H | H | F | H | H | SO₂Me | H | 425 |
| A-162 | Cl | CF₃ | H | H | Me | H | F | Cl | H | 395 |
| A-163 | Cl | CF₃ | H | H | Br | H | F | CF₃ | H | 493 |
| A-164 | Cl | CF₃ | H | H | Br | H | H | H | OCF₃ | 491 |
| A-165 | Cl | CF₃ | H | H | F | H | SMe | F | H | 411 |
| A-166 | Cl | CF₃ | H | H | CHCH₂ | H | H | F | H | 373 |
| A-167 | Cl | CF₃ | H | H | SMe | H | H | H | H | 375 |
| A-168 | Cl | CF₃ | H | H | F | H | SMe | Br | H | 471 |
| A-169 | Cl | CF₃ | H | H | H | H | I | OH | I | 597 |
| A-170 | Cl | CF₃ | H | H | CN | H | H | H | H | 354 |
| A-171 | Cl | CF₃ | H | H | OMe | H | H | NO₂ | H | 404 |
| A-172 | Cl | CF₃ | H | H | CF3 | H | H | H | F | 415 |
| A-173 | Cl | CF₃ | H | H | F | CF₃ | H | H | H | 415 |
| A-174 | Cl | CF₃ | H | H | F | I | H | H | H | 473 |
| A-175 | Cl | CF₃ | H | H | Br | H | H | H | F | 425 |
| A-176 | Cl | CF₃ | H | H | I | H | H | Cl | H | 489 |
| A-177 | Cl | CF₃ | H | H | I | H | H | H | Me | 469 |
| A-178 | Cl | CF₃ | H | H | Cl | H | Me | H | H | 377 |
| A-179 | Cl | CF₃ | H | H | I | H | Me | H | H | 469 |
| A-180 | Cl | CF₃ | H | H | Br | H | Me | H | H | 421 |
| A-181 | Cl | CF₃ | H | H | Cl | H | H | OMe | OMe | 423 |
| A-182 | Cl | CF₃ | H | H | F | Cl | Me | H | H | 395 |
| A-183 | Cl | CF₃ | H | H | I | H | H | H | Br | 533 |
| A-184 | Cl | CF₃ | H | H | Cl | H | H | H | Me | 377 |
| A-185 | Cl | CF₃ | H | H | Cl | H | H | H | I | 489 |
| A-186 | Cl | CF₃ | H | H | Me | H | H | H | F | 361 |
| A-187 | Cl | CF₃ | H | H | OCHF₂ | H | H | H | H | 395 |

TABLE A-continued

| Composé n° | X¹ | X² | X³ | X⁴ | Y¹ | Y² | Y³ | Y⁴ | Y⁵ | M + 1 |
|---|---|---|---|---|---|---|---|---|---|---|
| A-188 | Cl | CF₃ | H | H | I | H | H | H | Cl | 489 |
| A-189 | Cl | CF₃ | H | H | I | H | H | OMe | OMe | 515 |
| A-190 | Cl | CF₃ | H | H | Br | H | H | F | H | 425 |
| A-191 | Cl | CF₃ | H | H | CHF₂ | H | H | H | H | 422 |
| A-192 | Cl | CF₃ | H | H | S—CHF₂ | H | H | H | H | 411 |
| A-193 | Cl | CF₃ | H | H | Me | H | NH₂ | H | H | 358 |
| A-194 | Cl | CF₃ | H | H | NH₂ | H | Me | H | H | 358 |
| A-195 | Cl | CF₃ | H | H | iPr | H | H | H | H | 371 |
| A-196 | Cl | CF₃ | H | H | H | H | H | CF₃ | H | 397 |

TABLE B

| Composé n° | X¹ | X² | X³ | X⁴ | Y¹ | Y² | Y³ | Y⁴ | Y⁵ | M + 1 |
|---|---|---|---|---|---|---|---|---|---|---|
| B-1 | Cl | CF₃ | H | H | CF3 | H | H | H | H | 413 |
| B-2 | Cl | CF3 | H | H | OMe | H | H | H | H | 375 |
| B-3 | Cl | CF3 | H | H | F | F | H | Hl | Hl | 381 |
| B-4 | Cl | CF3 | H | H | Me | H | H | H | H | 359 |
| B-5 | Cl | CF3 | H | H | F | Cl | H | H | H | 398 |

The following examples of compound preparation are mentioned with the aim of illustrating the invention, but should in no way be considered to limit the said invention.

Preparation of methyl[3-chloro-5-(trifluoromethyl)-2-pyridinyl](cyano)acetate

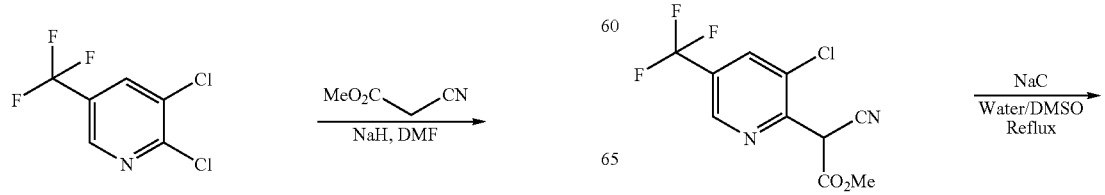

Procedure:

Under argon, 116 g of sodium hydride, 60% in dispersion in oil (2.91 mol, 1.8 eq.), are suspended in 3 L of DMF. The suspension is cooled in a bath of ice cold water. 160 g (1.616 mol, 1.0 eq.) of methyl cyanoacetate in solution in 200 mL of DMF are added dropwise, with stirring. Once all gas has been given off, 350 g (1.616 mol, 1.0 eq) of 2,3-dichloro-5-(trifluoromethyl)pyridine are added with stirring. The mixture is stirred overnight at ambient temperature. 50 mL of methanol are added. The reaction medium is poured into 5 L of water. The pH is adjusted to 3-4 with concentrated hydrochloric acid. The yellow precipitate of methyl [3-chloro-5-(trifluoromethyl)-2-pyridinyl](cyano)acetate which forms is filtered off and washed with water and with pentane.

Preparation of [3-chloro-5-(trifluoromethyl)-2-pyridinyl]acetonitrile

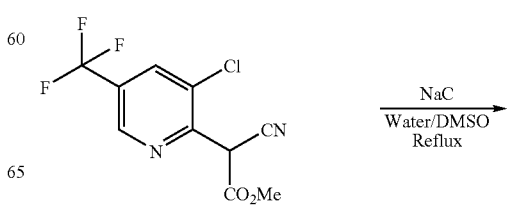

-continued

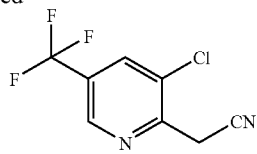

Procedure:

314 g (1.13 mol, 1 eq.) of methyl [3-chloro-5-(trifluoromethyl)-2-pyridinyl]-(cyano)acetate and 22 g (0.38 mol, 0.33 eq.) of sodium chloride are dissolved in a solution of 44 mL of water and 1.1 L of dimethyl sulphoxide. The reaction medium is stirred and heated at 160° C. Once all gas has been given off, the medium is cooled to ambient temperature. 1 L of water and 0.5 L of dichloromethane are added. After separation, the aqueous phase is extracted twice with 0.5 L of dichloromethane. The organic phase is washed twice with 0.5 L of water and dried over magnesium sulphate. After concentration, the crude product is diluted in 100 mL of dichloromethane and eluted with an ethyl acetate/heptane mixture (20/80) on a bed of silica. The filtrate is concentrated so as to produce [3-chloro-5-(trifluoromethyl)-2-pyridinyl]acetonitrile.

Preparation of 2-[3-chloro-5-(trifluoromethyl)-2-pyridinyl]ethanamine acetate

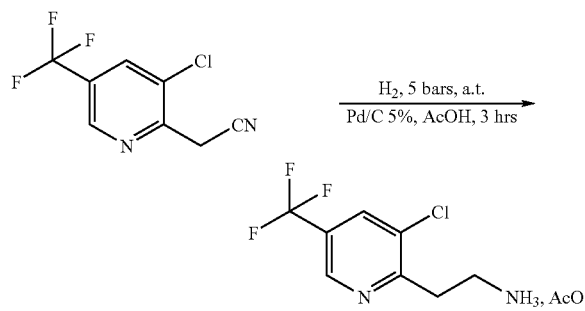

Procedure:

113 g of [3-chloro-5-(trifluoromethyl)-2-pyridinyl]acetonitrile (0.51 mol, 1 eq.) are diluted in 2.5 L of acetic acid. 30 g of palladium (5% on charcoal) are added. The reaction medium is stirred at ambient temperature under a hydrogen pressure of 5 bar. The progress of the reaction is followed by TLC; when the [3-chloro-5-(trifluoromethyl)-2-pyridinyl]acetonitrile has been completely used up, the medium is filtered over a bed of celite, and then concentrated to dryness so as to produce the 2-[3-chloro-5-(trifluoromethyl)-2-pyridinyl]ethanamine acetate.

Preparation of N-{2-[3-chloro-5-(trifluoromethyl)-2-pyridinyl]ethyl}-benzamides

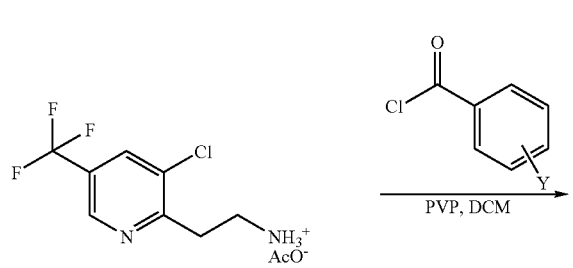

-continued

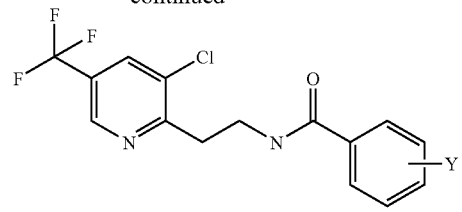

Procedure:

0.100 g of 2-[3-chloro-5-(trifluoromethyl)-2-pyridinyl]ethanamine acetate (0.00037 mol, 1.0 eq.) are diluted in 3 mL of dichloromethane. 0.500 g of poly(4-vinylpyridine) are added. The mixture is stirred at ambient temperature for half an hour.

1.2 equivalents of the desired acyl chloride are added. The reaction medium is stirred at ambient temperature overnight, filtered, and concentrated to dryness. The crude product is then purified by reverse-phase HPLC. The corresponding amide is obtained.

The following biological activities were tested in order to establish a comparison between the activity of the compounds of general formula (I) according to the present invention and a compound described in patent application WO 01/11965, on a certain number of fungal diseases.

In Vivo Test of Activity on *Alternaria brassicae* (Crucifer Black Spot)

An aqueous solution of the active material to be tested is prepared at a concentration of 2 g/l by grinding in solution 1 or solution 2:

Solution 1
  Water
  Tween 80 diluted to 10% in water: 5 µl/mg of active material
  Clay in a sufficient amount for active material+clay to equal 100 mg;

Solution 2
  Concentrated solution containing surfactants and adjuvants conventionally used: 200 µl/mg of active material.

The aqueous solution is diluted with water so as to obtain the desired concentration.

Radishes of the Pernot variety are sown in a 50/50 pozzolan/peat substrate and maintained at 18-22° C. The treatment is carried out by spraying the aqueous suspension. The untreated control plants are sprayed with water. 24 hours after treatment, the plants are inoculated by spraying a solution of *Alternaria brassicae* spores (40 000 spores/ml) originating from a 12-day culture.

The radish plants are then maintained at 18-20° C. in a humid atmosphere. The effectiveness of the products is evaluated relative to the control plants after seven to eight days of incubation.

In Vivo Test of Activity on *Botrytis cinerea* on Cucumber

An aqueous solution of the active material to be tested is prepared at a concentration of 2 g/l by grinding in solution 1 or solution 2:

Solution 1
  Water
  Tween 80 diluted to 10% in water: 5 µl/mg of active material
  Clay in a sufficient amount for active material+clay to equal 100 mg;

Solution 2

Concentrated solution containing surfactants and adjuvants conventionally used: 200 μl/mg of active material.

The aqueous solution is diluted with water so as to obtain the desired concentration.

Cucumbers of the Marketer variety are sown in a 50/50 pozzolan/peat substrate and maintained at 18-22° C. The treatment is carried out by spraying the aqueous suspension. The untreated control plants are sprayed with water.

24 hours after treatment, the plants are inoculated by spraying a solution of *Botrytis cinerea* spores (150 000 spores/ml) originating from a 15-day culture.

The cucumber plants are then maintained at 11-15° C. in a humid atmosphere. The effectiveness of the products is evaluated relative to the control plants after seven to eight days of incubation.

In Vivo Test of Activity on *Pyrenophora teres* (Barley Net Blotch)

An aqueous solution of the active material to be tested is prepared at a concentration of 2 g/l by grinding in solution 1 or solution 2:

Solution 1

Water

Tween 80 diluted to 10% in water: 5 μl/mg of active material

Clay in a sufficient amount for active material+clay to equal 100 mg;

Solution 2

Concentrated solution containing surfactants and adjuvants conventionally used: 200 μl/mg of active material.

The aqueous solution is diluted with water so as to obtain the desired concentration.

Barley plants of the Express variety are sown in a 50/50 pozzolan/peat substrate and maintained at 12° C. The treatment is carried out at the 1-leaf stage (10 cm) by spraying the aqueous suspension. The untreated control plants are sprayed with water.

24 hours after treatment, the plants are inoculated by spraying a solution of *Pyrenophora teres* spores (10 000 spores/ml) originating from a 10-day culture.

The barley plants are then maintained at 18° C. in a humid atmosphere. The effectiveness of the products is evaluated relative to the control plants after eight to fifteen days of incubation.

In Vivo Test of Activity on *Septoria tritici* (Wheat *Septoria* Disease

An aqueous solution of the active material to be tested is prepared at a concentration of 2 g/l by grinding in solution 1 or solution 2:

Solution 1

Water

Tween 80 diluted to 10% in water: 5 μl/mg of active material

Clay in a sufficient amount for active material+clay to equal 100 mg;

Solution 2

Concentrated solution containing surfactants and adjuvants conventionally used: 200 μl/mg of active material.

The aqueous solution is diluted with water so as to obtain the desired concentration.

Wheat plants of the Scipion variety are sown in a 50/50 pozzolan/peat substrate and maintained at 12° C. The treatment is carried out at the 1-leaf stage (10 cm) by spraying the aqueous suspension. The untreated control plants are sprayed with water.

24 hours after treatment, the plants are inoculated by spraying a solution of *Septoria tritici* spores (500 000 spores/ml) from a 7-day culture.

The wheat plantlets are then maintained at 18-20° C. in a humid atmosphere for 72 hours, and then at 90% relative humidity. The effectiveness of the products is evaluated relative to the control plants, 21 to 28 days after the contamination.

The effectiveness of the molecules is estimated, at 500 g/ha, 250 g/ha or 330 ppm, by the percentage of control relative to untreated plants. Under these conditions, good effectiveness is defined as more than 80% effectiveness. Average effectiveness is defined as an effectiveness between 50 and 80%. Poor effectiveness is defined as an effectiveness between 10 and 50% and zero effectiveness is defined as less than 10% effectiveness.

At a concentration of 500 g/ha, the following compounds showed good to average effectiveness against the fungal pathogens:

*Alternaria brassicae*: A-2, A-4, A-6, A-7, A-9, A-13, A-14, A-20, A-25.

*Botrytis cinerea*: A-2, A-7, A-9, A-20, A-25.

*Pyrenophora teres*: A-2, A-4, A-5, A-6, A-7, A-9, A-20, A-25, A-27.

*Septoria tritici*: A-2, A-4, A-5, A-6, A-7, A-16, A-18, A-20, A-21, A-22, A-23, A-24, A-25.

At a concentration of 250 g/ha, the following compounds showed good to average effectiveness against the fungal pathogens:

*Alternaria brassicae*: A-20, A-28, A-29, A-41, A-45, A-46, A-73, A-173.

*Botrytis cinerea*: A-20, A-45, A-46, A-73.

*Pyrenophora teres*: A-20, A-45, A-46, A-73.

At a concentration of 330 ppm, the following compounds showed good to average effectiveness against the fungal pathogens:

*Alternaria brassicae*: A-20, A-44, A-45, A-46, A-47, A-48, A-49, A-52, A-60, A-61, A-62, A-71, A-72, A-73, A-74, A-75, A-76, A-77, A-79, A-80, A-83, A-84, A-85, A-86, A-87, A-89, A-91, A-92, A-96, A-98, A-99, A-100, A-107, A-110, A-112, A-113, A-117, A-122, A-123, A-124, A-125, A-127, A-128, A-133, A-134, A-135, A-136, A-137, A-138, A-139, A-140, A-141, A-142, A-143, A-144, A-146, A-147, A-148, A-150, A-151, A-152, A-156, A-157, A-158, A-159, A-162, A-165, A-166, A-167, A-168, A-169, A-170, A-171, A-173, A-174, A-175, A-176, A-177, A-178, A-179, A-180, A-181, A-182, A-183, A-184, A-185, A-186, A-187, A-188, A-189, A-194, B-1.

*Botrytis cinerea*: A-20, A45, A-46, A-73, A-170, A-172, A-173, A-174, A-175, A-187.

*Pyrenophora teres*: A-20, A-44, A-45, A-46, A-61, A-73, A-83, A-87, A-89, A-96, A-117, A-125, A-133, A-134, A-140, A-167, A-173, A-174, A-187, B-1.

Under these conditions, the N-{2-[3-chloro-5-(trifluoromethyl)-2-pyridinyl]-ethyl}-2,6-dichlorobenzamide showed respectively poor and zero effectiveness on *Alternaria Brassicae* at 330 ppm and 250 g/ha; and zero effectiveness on *Botrytis cinerea* at 250 g/ha and 330 ppm.

Under these conditions, the N-{1-methylcarbamoyl-2-[3-chloro-5-(trifluoromethyl)-2-pyridinyl]ethyl}-4-phenylbenzamide disclosed by Patent Application WO 01/11965 (see compound 316 in Table D) showed poor effectiveness on *Alternaria Brassicae* and *Septoria tritici*, and zero effectiveness on *Botrytis cinerea* at 250 g/ha; the N-{1-ethylcarbamoyl-2-[3-chloro-5-(trifluoromethyl)-2-pyridinyl]ethyl}-3-nitrobenzamide also disclosed by patent application WO 01/11965 (see compound 307 in table D) showed zero effectiveness on *Alternaria brassicae* and *Botrytis cinerea* at 250 g/ha; the N-{1-ethylcarbamoyl-2-[3-chloro-5-(trifluoromethyl)-2-pyridinyl]ethyl}-benzamide and the N-{1-methylcarbamoyl-2-[3-chloro-5-(trifluoromethyl)$_2$-pyridinyl]ethyl}-benzamide also disclosed by patent application WO 01/11965 (see compounds 304 and 314 in table d) showed poor effectiveness on *Septoria tritici* and zero effectiveness on *Botrytis cinerea* at 250 g/ha; and the N-{1-ethylcarbamoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-2-bromobenzamide and the N-{1-methylcarbamoyl-2-[3-chloro-5-(trifluoromethyl)-2-pyridinyl]ethyl}-4-methoxybenzamide also disclosed by patent application WO 01/11965 (see compounds 306, 310 and 315 in table D) showed zero effectiveness on *Botrytis cinerea* at 250 g/ha.

The invention claimed is:

1. A compound of the general formula (I):

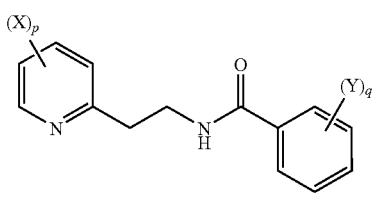

(I)

wherein p is an integer equal to 1, 2, 3 or 4;

q is an integer equal to 1, 2, 3, 4 or 5;

each X is independently selected from the group consisting of halogen, alkyl, and haloalkyl, provided that at least one X is a haloalkyl;

each Y is independently selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulphonyl, halothioalkyl, alkoxyalkenyl, alkylsulphonamide, nitro, alkylsulphonyl, phenylsulphonyl, and benzylsulphonyl;

as to the N-oxides of 2-pyridine thereof;

with the exception of N-{2-[3-chloro-5-(trifluoromethyl)-2-pyridinyl]ethyl}-2,6-dichlorobenzamide.

2. The compound of claim 1 wherein p is equal to 2.

3. The compound of claim 1 wherein q is chosen equal to 1 or 2, the substituent(s) Y being positioned in the ortho position of the benzene ring.

4. The compound of claim 3 wherein said compound corresponds to the general formula (I'):

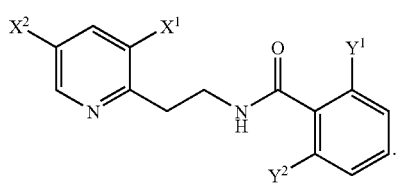

(I')

5. The compound of claim 4 wherein $X^1$ is halogen and $X^2$ is haloalkyl.

6. The compound of claim 3 wherein said compound corresponds to the general formula (I"):

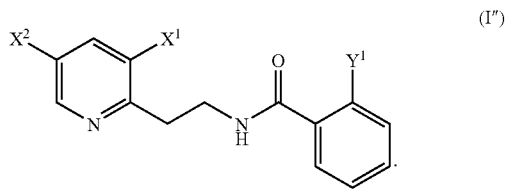

(I")

7. A compound selected from the group consisting of N-{2-[3-chloro-5-(trifluoromethyl)-2-pyridinyl]ethyl}-2-trifluoromethylbenzamide;

-{2-[3-chloro-5-(trifluoromethyl)-2-pyridinyl]ethyl}-2-iodobenzamide; and

-{2-[3-chloro-5-(trifluoromethyl)-2-pyridinyl]ethyl}-2-bromobenzamide.

8. The compound 6 wherein said compound has the following characteristics, taken individually or in combination:

$X^1$ is halogen and $X^2$ is haloalkyl;

$Y^1$ is selected from the group consisting of halogen and haloalkyl.

9. The compound of claim 8 wherein the haloalkyl group is trifluoromethyl.

10. A process for the preparation of compounds of general formula (I):

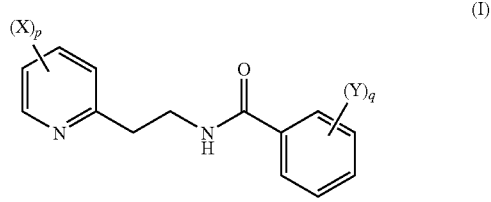

(I)

wherein p is an integer equal to 1, 2, 3 or 4;

q is an integer equal to 1, 2, 3, 4 or 5;

each X is independently selected from the group consisting of halogen, alkyl, and haloalkyl, provided that at least on X is a haloalkyl;

each Y is independently selected from the group consisting of halogen, alkyl, alkenyl, alkynyl, haloalkyl, alkoxy, amino, phenoxy, alkylthio, dialkylamino, acyl, cyano, ester, hydroxy, aminoalkyl, benzyl, haloalkoxy, halosulphonyl, halothioalkyl, alkoxyalkenyl, alkylsulphonamide, nitro, alkysulphonyl, phenylsulphonyl, and benzylsulphonyl;

as to the N-oxides of 2-pyridine thereof;

with the exception of N-{2-[3-chloro-5-(trifluoromethyl)-2-pyridinyl]ethyl}-2,6-dichlorobenzamide;

wherein said process comprises:

(A) reacting, in the presence of a base in a protic polar solvent, a compound of general formula (Ia)

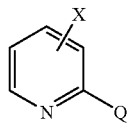
(Ia)

in order to substitute it selectively in the 2- position:
(1) with NC—CH$_2$—CO$_2$Alk to produce a compound of general formula (Ib)

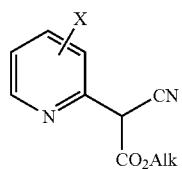
(Ib)

wherein:
X is as defined above;
Alk represents an alkyl radical;
Q is a nucleofugal radical;
which is caused to undergo dealkyloxycarbonylation in the presence of an alkali metal halide at the reflux of a water/dimethyl sulphoxide mixture to produce a compound of general formula (Ic)

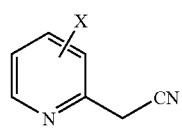
(Ic)

or
(2) with acetonitrile to produce the compound (Ic) directly;
(B) reducing compound (Ic) to a pyridylethanamine of general formula (Id)

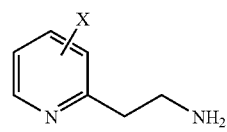
(Id)

or its corresponding ammonium salt under hydrogen pressure in the presence of a metal catalyst in a protic solvent;
(C) reacting compound (Id) or its corresponding ammonium salt with a benzoyl halide of general formula (Ie)

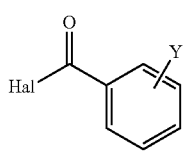
(Ie)

wherein Y is as defined above,
in the presence of a base to provide the compound of general formula (I).

11. The process of claim 10 wherein the nucleofugal radical Q is selected from the group consisting of a halogen or and trifluoromethanesulphonate.

12. A fungicidal composition comprising an effective amount of a compound according to claim 1 and an agriculturally acceptable support.

13. The fungicidal composition of claim 12 further comprising a surfactant.

14. The fungicidal composition of claim 12 comprising from 0.05% to 99% by weight of active material.

15. A method for preventively or curatively combating the phytopathogenic fungi of plants, wherein said fungi are selected from the group consisting of *Alternaria brassicae, Botrytis cinerea, Pyrenophora teres*, and *Septoria tritici*, comprising applying an effective and non-phytotoxic amount of a fungicidal composition comprising a compound of the general formula(I")

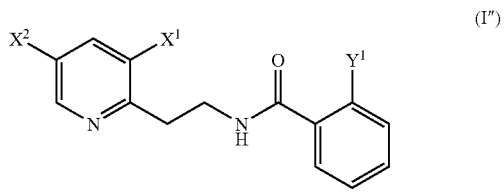
(I")

and an agriculturally acceptable support to:
(A) the plant seeds,
(B) the plant leaves,
(C) the fruits of the plants,
(D) a combination of (B) and (C), or
(E) to the soil in which the plants are growing or in which it is desired to grow them;
wherein
X$^1$ and X$^2$ are independently selected from the group consisting of halogen, alkyl, and haloalkyl, provided that at least one of X$^1$ and X$^2$ is a haloalkyl; and
Y$^1$ is selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulphonyl, halothioalkyl, alkoxyalkenyl, alkylsulphonamide, nitro, alkylsulphonyl, phenylsulphonyl, and benzylsulphonyl.

16. The compound of claim 2 wherein the substituents X are positioned as follows:

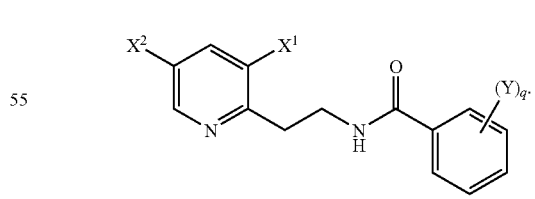

* * * * *

UNITED STATES PATENT AND TRADEMARK OFFICE
CERTIFICATE OF CORRECTION

PATENT NO. : 7,572,818 B2　　　　　　　　　　　　　　　　　　　　　　　Page 1 of 1
APPLICATION NO. : 10/524345
DATED : August 11, 2009
INVENTOR(S) : Mansfield et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 830 days.

Signed and Sealed this

Seventh Day of September, 2010

David J. Kappos
*Director of the United States Patent and Trademark Office*